(12) United States Patent
Ramakrishna et al.

(10) Patent No.: US 8,143,303 B2
(45) Date of Patent: Mar. 27, 2012

(54) CARBAZOLE DERIVATIVES AS FUNCTIONAL 5-HT$_6$ LIGANDS

(75) Inventors: Venkata Satya Nirogi Ramakrishna, Andhra Pradesh (IN); Rama Sastri Kambhampati, Andhra Pradesh (IN); Vikas Shreekrishna Shirsath, Andhra Pradesh (IN); Jagadish Babu Konda, Andhra Pradesh (IN); Santosh Vishwakarma, Andhra Pradesh (IN); Venkateswarlu Jasti, Andhra Pradesh (IN)

(73) Assignee: Suven Life Sciences Limited, Andhra Pradesh (IN)

( * ) Notice: Subject to any disclaimer, the term of this patent is extended or adjusted under 35 U.S.C. 154(b) by 341 days.

(21) Appl. No.: 12/083,707

(22) PCT Filed: Jun. 9, 2006

(86) PCT No.: PCT/IN2006/000195
§ 371 (c)(1),
(2), (4) Date: Apr. 1, 2010

(87) PCT Pub. No.: WO2007/046111
PCT Pub. Date: Apr. 26, 2007

(65) Prior Publication Data
US 2010/0189646 A1    Jul. 29, 2010

(30) Foreign Application Priority Data
Oct. 19, 2005 (IN) .......................... 1504/CHE/2005

(51) Int. Cl.
*A61K 31/403* (2006.01)
*C07D 209/88* (2006.01)
(52) U.S. Cl. ...................................... 514/411; 548/439
(58) Field of Classification Search .................. 548/439; 514/411
See application file for complete search history.

(56) References Cited

OTHER PUBLICATIONS

Geldenhuys et al., Current Topics in Medicinal Chemistry 2008, 8(12), 1035-1048.*
Schafer et al., Drug Discovery Today 2008, 13 (21/22), 913-916.*
Horig et al., Journal of Translational Medicine 2004, 2(44).*
Kulka et al., Journal of Organic Chemistry 1952, 17, 1501-04.*
International Search Report in respect of counterpart PCT Application No. IN2006/000195.
Chang-Fong, Jean, et al., "1,2,3-4-Tetrahydrocarbazoles as 5H$_6$Tserotonin receptor ligands", *Bioorganic and Medicinal Chemistry Letters*, vol. 14, 2004, pp. 1961-1964.
Lee, Mase, et al., "5HT$_6$ Serotonin Receptor Binding Affinities of $_1$NBenzenesulfonyl and Related Tryptamines", *Medicinal Chemistry Research*, vol. 10, No. 4, 2000, pp. 230-242.

* cited by examiner

*Primary Examiner* — Jason M Nolan
(74) *Attorney, Agent, or Firm* — Ladas & Parry LLP

(57) ABSTRACT

Carbazole derivatives of formula (I), useful in treatment of a CNS disorders related to or affected by the 5-HT$_6$ receptor are described. The pharmacological profile of these compounds includes high affinity binding with 5-HT$_6$ receptor along with good selectivity towards the receptor. Stereoisomers, the salts, methods of preparation and medicines containing the carbazole derivatives are also described.

13 Claims, No Drawings

CARBAZOLE DERIVATIVES AS FUNCTIONAL 5-HT$_6$ LIGANDS

FIELD OF INVENTION

The present invention relates to certain carbazole derivatives, their stereoisomers, their salts, their preparation and medicines containing them.

BACKGROUND OF THE INVENTION

Various central nervous system disorders such as anxiety, depression, motor disorders etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. 5-HT receptor subtypes regulate the various effects of serotonin. Known 5-HT receptor family includes the 5-HT$_1$ family (e.g. 5-HT$_{1A}$), the 5-HT$_2$ family (e.g. 5-HT$_{2A}$), 5-HT$_3$, 5-HT$_4$, 5-HT$_5$, 5-HT$_6$ and 5-HT$_7$ subtypes.

The 5-HT$_6$ receptor subtype was first cloned from rat tissue in 1993 (Monsma, F. J.; Shen, Y.; Ward, R. P.; Hamblin, M. W., Molecular Pharmacology, 1993, 43, 320-327) and subsequently from human tissue (Kohen, R.; Metcalf; M. A.; Khan, N.; Druck, T.; Huebner, K.; Sibley, D. R., Journal of Neurochemistry, 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C., Biochemical Biophysical Research Communications, 1993, 193, 268-276). The receptor is found almost exclusively in the central nervous system (CNS) areas both in rat and in human.

In situ hybridization studies of the 5-HT$_6$ receptor in rat brain rising mRNA indicate principal localization in the areas of 5-HT projection including striatum, nucleus accumbens, olfactory tubercle and hippocampal formation (Ward, R. P.; Hamblin, M. W.; Lachowicz, J. E.; Hoffman, B. J.; Sibley, D. R.; Dorsa, D. M., Neuroscience, 1995, 64, 1105-1111). Highest levels of 5-HT$_6$ receptor mRNA has been observed in the olfactory tubercle, the striatum, nucleus accumbens, dentate gyrus as well as CA$_1$, CA$_2$ and CA$_3$ regions of the hippocampus. Lower levels of 5-HT$_6$ receptor mRNA were seen in the granular layer of the cerebellum, several diencephalic nuclei, amygdala and in the cortex. Northern blots have revealed that 5-HT$_6$ receptor mRNA appears to be exclusively present in the brain, with little evidence for its presence in peripheral tissues.

The high affinity of a number of antipsychotic agents for the 5-HT$_6$ receptor, in addition to its mRNA localization in striatum, olfactory tubercle and nucleus accumbens suggests that some of the clinical actions of these compounds may be mediated through this receptor. Its ability to bind a wide range of therapeutic compounds used in psychiatry, coupled with its intriguing distribution in the brain has stimulated significant interest in new compounds which are capable of interacting with or affecting the said receptor. At present, there are no known fully selective agonists. Significant efforts are being made to understand the possible role of the 5-HT$_6$ receptor in psychiatry, cognitive dysfunction, motor function and control, memory, mood and the like. To that end, compounds which demonstrate a binding affinity for the 5-HT$_6$ receptor are earnestly sought both as an aid in the study of the 5-HT$_6$ receptor and as potential therapeutic agents in the treatment of central nervous system disorders, for example see C. Reavill and D. C. Rogers, Current Opinion in Investigational Drugs, 2001, 2(1):104-109, Pharma Press Ltd.

There are many potential therapeutic uses for 5-HT$_6$ ligands in humans based on direct effects and on indications from available scientific studies. These studies include the localization of the receptor, the affinity of ligands with known in vivo activity, and various animal studies conducted so far. Preferably, antagonist compounds of 5-HT$_6$ receptors are sought after as therapeutic agents. One potential therapeutic use of modulators of 5-HT$_6$ receptor function is in the enhancement of cognition and memory in human diseases such as Alzheimer's. The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miguel, M. C.; Verge, D.; Lanfumey, R.; Doucet, E.; Hamon, M.; E I Mestikawy, S., Brain Research, 1997, 746, 207-219). The ability of known 5-HT$_6$ receptor ligands to enhance cholinergic transmission also supported the potential cognition use (Bentey, J. C.; Boursson, A.; Boess, F. G.; Kone, F. C.; Marsden, C. A.; Petit, N.; Sleight, A. J., British Journal of Pharmacology, 1999, 126 (7), 1537-1542).

Studies have found that a known 5-HT$_6$ selective antagonist significantly increased glutamate and aspartate levels in the frontal cortex without elevating levels of noradrenaline, dopamine, or 5-HT. This selective elevation of neurochemicals known to be involved in memory and cognition strongly suggests a role for 5-HT$_6$ ligands in cognition (Dawson, L. A.; Nguyen, H. Q.; Li, P. British Journal of Pharmacology, 2000, 130 (1), 23-26). Animal studies of memory and learning with a known selective 5-HT$_6$ antagonist found some positive effects (Rogers, D. C.; Hatcher, P. D.; Hagan, J. J. Society of Neuroscience, Abstracts, 2000, 26, 680).

A related potential therapeutic use for 5-HT$_6$ ligands is the treatment of attention deficit disorders (ADD, also known as Attention Deficit Hyperactivity Disorder or ADHD) in both children and adults. Because 5-HT$_6$ antagonists appear to enhance the activity of the nigrostriatal dopamine pathway and because ADHD has been linked to abnormalities in the caudate (Ernst, M; Zametkin, A. J.; Matochik, J. H.; Jons, P. A.; Cohen, R. M., Journal of Neuroscience, 1998, 18(15), 5901-5907), 5-HT$_6$ antagonists may attenuate attention deficit disorders.

International Patent Publication WO 03/066056 A1 reports that antagonism of 5-HT$_6$ receptor could promote neuronal growth within the central nervous system of a mammal. Another International Patent Publication WO 03/065046 A2 discloses new variant of human 5-HT$_6$ receptor, and proposes that human 5-HT$_6$ receptor is being associated with numerous other disorders.

Early studies examining the affinity of various CNS ligands with known therapeutic utility or a strong structural resemblance to known drugs suggests a role for 5-HT$_6$ ligands in the treatment of schizophrenia and depression. For example, clozapine (an effective clinical antipsychotic) has high affinity for the 5-HT$_6$ receptor subtype. Also, several clinical antidepressants have high affinity for the receptor as well and act as antagonists at this site (Branchek, T. A.; Blackburn, T. P., Annual Reviews in Pharmacology and Toxicology, 2000, 40, 319-334).

Further, recent in vivo studies in rats indicate that 5-HT$_6$ modulators may be useful in the treatment of movement disorders including epilepsy (Stean, T.; Routledge, C.; Upton, N., British Journal of Pharmacology, 1999, 127 Proc. Supplement-131P; and Routledge, C.; Bromidge, S. M.; Moss, S. F.;

Price, G. W.; Hirst, W.; Newman, H.; Riley, G.; Gager, T.; Stean, T.; Upton, N.; Clarke, S. E.; Brown, A. M., British Journal of Pharmacology, 2000, 30 (7), 1606-1612).

Taken together, the above studies strongly suggest that compounds which are 5-$HT_6$ receptor modulators, i.e. ligands, may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g. anxiety, depression and obsessive compulsive disorders; the treatment of motion or motor disorders such as Parkinson's disease and epilepsy; the treatment of diseases associated with neurodegeneration such as stroke or head trauma; or withdrawal from drug addiction including addiction to nicotine, alcohol, and other substances of abuse.

Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, 1). R. Sibley et al., Molecular Pharmacology, 1993, 43, 320-327, A. J. Sleight et al., Neurotransmission, 1995, 11, 1-5, and A. J. Sleight et al., Serotonin ID Research Alert, 1997, 2(3), 115-118.

Furthermore, the effect of 5-$HT_6$ antagonist and 5-$HT_6$ antisense oligonucleotides to reduce food intake in rats has been reported thus potentially in treatment of obesity. See for example, Bentley et al., British Journal of Pharmacology, 1999, Suppl., 126, A64: 255; Wooley et al., Neuropharmacology, 2001, 41: 210-129; and WO 02/098878.

International Patent Publications WO 2004/055026 A1, WO 2004/048331 A1, WO 2004/048330 A1 and WO 2004/048328 A2 (all assigned to Suven Life Sciences Limited) describes related prior art. Further WO 98/27081, WO 99/02502, WO 99/37623, WO 99/42465 and WO01/32646 (all assigned to Glaxo SmithKline Beecham PLC) disclose a series of aryl sulphonamide and sulphoxide compounds as 5-$HT_6$ receptor antagonists and which are claimed to be useful in the treatment of various CNS disorders. While some 5-$HT_6$ modulators have been disclosed, there continues to be a need for compounds that are useful for modulating 5-$HT_6$.

Therefore, it is an object of this invention to provide compounds, which are useful as therapeutic agents in the treatment of a variety of central nervous system disorders related to or affected by the 5-$HT_6$ receptor functions.

It is another object of this invention to provide therapeutic methods and pharmaceutical compositions useful for the treatment of central nervous system disorders related to or affected by the 5-$HT_6$ receptor.

It is a feature of this invention that the compounds provided may also be used to further study and elucidate the 5-$HT_6$ receptor.

The preferred object of the invention is to synthesize a potent selective 5-$HT_6$ receptor antagonist.

SUMMARY OF THE INVENTION

Carbazole class of compounds have now been found which demonstrate 5-$HT_6$ receptor affinity, which may be used as effective therapeutic agents for the treatment of central nervous system (CNS) disorders.

(i) The present invention relates to a compound of the Formula (I), along with its stereoisomer or its salt with an inorganic or organic acid,

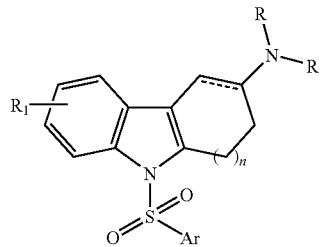

Formula (I)

or a pharmaceutically acceptable salt thereof wherein: '- - -' dashed line represents optional double bond; Ar represents any one group selected from phenyl, naphthyl, monocyclic or bicyclic heteroaryl, each of which may be further substituted by one or more independent substituents are defined as $R_1$; Ar— for example may be,

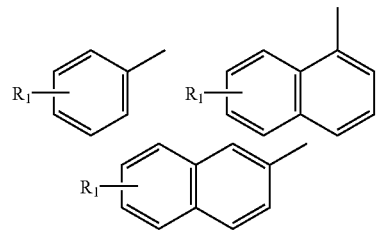

$R_1$ represents one or multiple substitutions on the benzene ring, and includes a hydrogen, halogen, cyano, ($C_1$-$C_3$) alkyl, halo($C_1$-$C_3$)alkyl, ($C_1$-$C_3$)alkoxy, halo($C_1$-$C_3$) alkoxy, cyclo($C_3$-$C_6$)alkyl or cyclo($C_3$-$C_6$)alkoxy; R represents either hydrogen or ($C_1$-$C_3$)alkyl; and "n" represents integer either 1 or 2.

The present invention also provides methods for preparing, compositions comprising, and methods for using Compounds of Formula (I).

(ii) In another aspect, the invention relates to pharmaceutical compositions containing a therapeutically effective amount of at least one compound of formula (I), or individual stereoisomers, racemic or non-racemic mixture of stereoisomers, or pharmaceutically acceptable salts or solvates thereof, in admixture with at least one suitable carrier.

(iii) In another aspect, the invention relates to the use of a therapeutically effective amount of compound of formula (I), in manufacture of a medicament, for the treatment or prevention of a disorders involving selective affinity for the 5-$HT_6$ receptor.

(iv) In another aspect, the invention further relates to the process for preparing compounds of formula (I).

(v) Partial list of such compounds of general formula (I) is as follows:

(9-Benzenesulfonyl-2,3,4,9-tetrahydro-1H-carbazol-3-yl) dimethylamine;

9-[(4-Bromobenzenesulphonyl)-2,3,4,9-tetrahydro-1H-carbazol-3-yl]dimethylamine;

9-[(4-Fluorobenzenesulphonyl)-2,3,4,9-tetrahydro-1H-carbazol-3-yl]dimethylamine;

9-[(4-Methylbenzenesulfonyl)-2,3,4,9-tetrahydro-1H-carbazol-3-yl]dimethylamine;

[9-(3-Chlorobenzenesulfonyl)-2,3,4,9-tetrahydro-1H-carbazol-3-yl]dimethylamine;

[9-(4-Isopropylbenzenesulfonyl)-2,3,4,9-tetrahydro-1H-carbazol-3-yl]dimethylamine;

[9-(3-Trifluoromethylbenzenesulfonyl)-2,3,4,9-tetrahydro-1H-carbazol-3-yl]dimethylamine;
[9-(4-Methoxybenzenesulfonyl)-2,3,4,9-tetrahydro-1H-carbazol-3-yl]dimethylamine;
[6-Bromo-9-(benzenesulphonyl)-2,3,4,9-tetrahydro-1H-carbazol-3-yl]dimethylamine;
[6-Bromo-9-(4-bromobenzenesulphonyl)-2,3,4,9-tetrahydro-1H-carbazol-3-yl]dimethylamine;
[6-Bromo-9-(4-fluorobenzenesulphonyl)-2,3,4,9-tetrahydro-1H-carbazol-3-yl]dimethylamine;
[6-Bromo-9-(4-isopropylbenzenesulphonyl)-2,3,4,9-tetrahydro-1H-carbazol-3-yl]dimethylamine;
[6-Bromo-9-(3-trifluoromethylbenzenesulphonyl)-2,3,4,9-tetrahydro-1H-carbazol-3-yl]dimethylamine;
[6-Bromo-9-(2-bromobenzenesulphonyl)-2,3,4,9-tetrahydro-1H-carbazol-3-yl]dimethylamine;
[6-Bromo-9-(4-methoxybenzenesulphonyl)-2,3,4,9-tetrahydro-1H-carbazol-3-yl]dimethylamine;
[6-Chloro-9-benzenesulfonyl-2,3,4,9-tetrahydro-1H-carbazol-3-yl]dimethylamine;
[6-Chloro-9-(3-trifluoromethylbenzenesulfonyl)-2,3,4,9-tetrahydro-1H-carbazol-3-yl]dimethylamine;
[6-Chloro-9-(4-methylbenzenesulfonyl)-2,3,4,9-tetrahydro-1H-carbazol-3-yl]dimethylamine;
[6-Chloro-9-(4-bromobenzenesulfonyl)-2,3,4,9-tetrahydro-1H-carbazol-3-yl]dimethylamine;
[6-Chloro-9-(4-fluorobenzenesulfonyl)-2,3,4,9-tetrahydro-1H-carbazol-3-yl]dimethylamine;
[6-Fluoro-9-benzenesulfonyl-2,3,4,9-tetrahydro-1H-carbazol-3-yl]dimethylamine;
[6-Fluoro-9-(4-methylbenzenesulfonyl)-2,3,4,9-tetrahydro-1H-carbazol-3-yl]dimethylamine;
[6-Fluoro-9-(4-isopropylbenzenesulfonyl)-2,3,4,9-tetrahydro-1H-carbazol-3-yl]dimethylamine;
[6-Fluoro-9-(4-bromobenzenesulfonyl)-2,3,4,9-tetrahydro-1H-carbazol-3-yl]dimethylamine;
[6-Fluoro-9-(4-fluorobenzenesulfonyl)-2,3,4,9-tetrahydro-1H-carbazol-3-yl]dimethylamine;
[6-Methoxy-9-benzenesulfonyl-2,3,4,9-tetrahydro-1H-carbazol-3-yl]dimethylamine;
[6-Methoxy-9-(4-methylbenzenesulfonyl)-2,3,4,9-tetrahydro-1H-carbazol-3-yl]dimethylamine;
[6-Methoxy-9-(4-methoxybenzenesulfonyl)-2,3,4,9-tetrahydro-1H-carbazol-3-yl]dimethylamine;
[6-Methoxy-9-(4-bromobenzenesulfonyl)-2,3,4,9-tetrahydro-1H-carbazol-3-yl]dimethylamine;
[6-Methoxy-9-(4-fluorobenzenesulfonyl)-2,3,4,9-tetrahydro-1H-carbazol-3-yl]dimethylamine;
[6-Methoxy-9-(3-trifluoromethylbenzenesulfonyl)-2,3,4,9-tetrahydro-1H-carbazol-3-yl]dimethylamine;
[6-Methylthio-9-benzenesulfonyl-2,3,4,9-tetrahydro-1H-carbazol-3-yl]dimethylamine;
[6-Methylthio-9-(4-methylbenzenesulfonyl)-2,3,4,9-tetrahydro-1H-carbazol-3-yl]dimethylamine;
[6-Methylthio-9-(4-bromobenzenesulfonyl)-2,3,4,9-tetrahydro-1H-carbazol-3-yl]dimethylamine;
[6-Methylthio-9-(4-Fluorobenzenesulfonyl)-2,3,4,9-tetrahydro-1H-carbazol-3-yl]dimethylamine;
[6-Chloro-9-(2-bromobenzenesulfonyl)-2,3,4,9-tetrahydro-1H-carbazol-3-yl]dimethylamine;
[6,8-Difluoro-9-(4-methylbenzenesulfonyl)-2,3,4,9-tetrahydro-1H-carbazol-3-yl]dimethylamine;
[6,8-Difluoro-9-(benzenesulfonyl-2,3,4,9-tetrahydro-1H-carbazol-3-yl]dimethylamine;
[6-Bromo-9-(2,3-dichlorobenzenesulphonyl)-2,3,4,9-tetrahydro-1H-carbazol-3-yl]dimethylamine;
[6-Methylthio-9-(2,3-dichlorobenzenesulfonyl-2,3,4,9-tetrahydro-1H-carbazol-3-yl]dimethylamine;
[6-Methylthio-9-(4-methoxybenzenesulfonyl-2,3,4,9-tetrahydro-1H-carbazol-3-yl]dimethylamine;
[6-Methylthio-9-(3-chlorobenzenesulfonyl-2,3,4,9-tetrahydro-1H-carbazol-3-yl]dimethylamine; a stereoisomer thereof; and a salt thereof.

DETAILED DESCRIPTION OF THE INVENTION

The 5-hydroxytryptamine-6 (5-$HT_6$) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor.

Surprisingly, it has now been found that carbazole derivatives of formula (I) demonstrate 5-$HT_6$ receptor affinity,

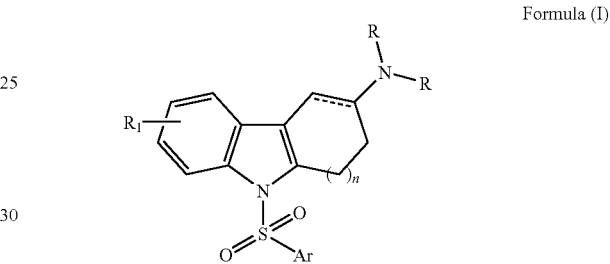

Formula (I)

including its stereoisomer or its salt with an inorganic or organic acid, wherein: '----' dashed line represents optional double bond; Ar represents any one group selected from phenyl, naphthyl, monocyclic or bicyclic heteroaryl, each of which may be further substituted by one or more independent substituents as defined by $R_1$; Ar— for example may be,

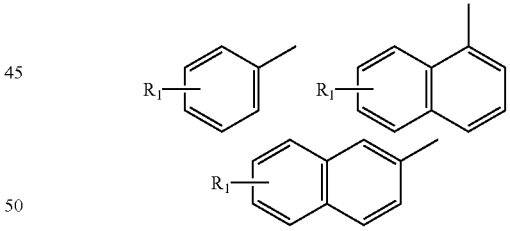

$R_1$ represents one or multiple substitutions on the benzene ring, and includes a hydrogen, halogen, cyano, ($C_1$-$C_3$) alkyl, halo($C_1$-$C_3$)alkyl, ($C_1$-$C_3$)alkoxy, halo($C_1$-$C_3$) alkoxy, cyclo($C_3$-$C_6$)alkyl or cyclo($C_3$-$C_6$)alkoxy; R represents either hydrogen or ($C_1$-$C_3$)alkyl; and "n" represents integer either 1 or 2.

Each group of compound (I) is explained below. Each term used herein is defined to have meanings described below in either case of a single or a joint use with other terms, unless otherwise noted.

The term "halogen" as used herein and in the claims (unless the context indicates otherwise) means atom such as fluorine, chlorine, bromine or iodine;

The term "($C_1$-$C_3$)alkyl" as used herein and in the claims (unless the context indicates otherwise) means straight and branched chain alkyl radicals containing from one to three carbon atoms and includes methyl, ethyl, n-propyl and iso-propyl.

The term "$(C_1-C_3)$alkoxy" as used herein and in the claims (unless the context indicates otherwise) means straight and branched chain alkoxy radicals containing from one to three carbon atoms and includes methoxy, ethoxy, propyloxy and iso-propyloxy, which may be further substituted.

The term "halo$(C_1-C_3)$alkyl" as used herein and in the claims (unless the context indicates otherwise) means straight and branched chain alkyl radicals containing from one to three carbon atoms and includes fluoromethyl, difluoromethyl, trifluoromethyl, trifluoroethyl, fluoroethyl, difluoroethyl and the like.

The term "halo$(C_1-C_3)$alkoxy" as used herein and in the claims (unless the context indicates otherwise) means straight and branched chain alkoxy radicals containing from one to three carbon atoms and includes fluoromethoxy, difluoromethoxy, trifluoromethoxy, trifluoroethoxy, fluoroethoxy, difluoroethoxy and the like.

The term "cyclo$(C_3-C_6)$alkyl" as used herein and in the claims (unless the context indicates otherwise) means cyclic alkyl radicals containing from three to six carbon atoms and includes cyclopropyl, cyclobutyl, cyclopentyl, cyclohexyl, the cycloalkyl group may be substituted.

The term "cyclo$(C_3-C_6)$alkoxy" as used herein and in the claims (unless the context indicates otherwise) means cyclic alkoxy radicals containing from three to six carbon atoms and includes cyclopropyloxy, cyclobutyloxy, cyclopentyloxy, cyclohexyloxy, the cycloalkoxy group may be substituted and the like.

The term "heteroaryl" is intended to mean a 5 or 6 membered monocyclic aromatic or a fused 8-10 membered bicyclic aromatic ring containing 1 to 3 heteroatoms selected from oxygen, nitrogen and sulphur. Suitable examples of such monocyclic aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such fused aromatic rings, include benzofused aromatic rings such as quinolinyl, isoquinolinyl, quinazolinyl, quinoxalinyl, cinnolinyl, naphthyridinyl, indolyl, isoindolyl, indazolyl, pyrrolopyridinyl, benzofuranyl, isobenzofuranyl, benzothienyl, benzimidazolyl, benzoxazolyl, benzisoxazolyl, benzothiazolyl, benzisothiazolyl, benzoxadiazolyl, benzothiadiazolyl, benzotriazolyl and the like. Heteroaryl groups, as described above, may be linked to the remainder of the molecule via a carbon atom or, when present, a suitable nitrogen atom except where otherwise indicated above. It will be appreciated that wherein the above mentioned aryl or heteroaryl groups have more than one substituent, said substituents may be linked to form a ring, for example a carboxyl and amine group may be linked to form an amide group.

The term 5- to 7-membered heterocyclic ring is intended to mean a non aromatic ring containing 1 to 3 heteroatoms selected from oxygen, nitrogen and sulphur. Such rings may be partially unsaturated. Suitable examples of 5- to 7-membered heterocyclic rings include piperidinyl, tetrahydropyridinyl, pyrrolidinyl, morpholinyl, azepanyl, diazepanyl and piperazinyl. A 5- to 7-membered heterocyclic ring, as described above, may be linked to the remainder of the molecule via a carbon atom or a suitable nitrogen atom.

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The term "stereoisomers" is a general term for all isomers of the individual molecules that differ only in the orientation of their atoms in space. It includes mirror image isomers (enantiomers), geometric (cis-trans) isomers and isomers of compounds with more than one chiral centre that are not mirror images of one another (diastereomers).

The stereoisomers as a rule are generally obtained as racemates that can be separated into the optically active isomers in a manner known per se. In the case of the compounds of general formula (I) having an asymmetric carbon atom the present invention relates to the D-form, the L-form and D,L-mixtures and in the case of a number of asymmetric carbon atoms, the diastereomeric forms and the invention extends to each of these stereoisomeric forms and to mixtures thereof including racemates. Those compounds of general formula (I) which have an asymmetric carbon and as a rule are obtained as racemates can be separated one from the other by the usual methods, or any given isomer may be obtained by stereospecific or asymmetric synthesis. However, it is also possible to employ an optically active compound from the start, a correspondingly optically active or diastereomeric compound then being obtained as the final compound.

The stereoisomers of compounds of general formula (I) may be prepared by one or more ways presented below:

i) One or more of the reagents may be used in their optically active form.

ii) Optically pure catalyst or chiral ligands along with metal catalyst may be employed in the reduction process. The metal catalysts may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).

iii) The mixture of stereoisomers may be resolved by conventional methods such as forming a diastereomeric salts with chiral acids or chiral amines, or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).

iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino group such as lysine, arginine and the like. In the case of the compounds of general formula (I) containing geometric isomerism the present invention relates to all of these geometric isomers.

Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluene-sulfonic, methanesulfonic or naphthalenesulfonic acid. The present invention includes within its scope all possible stoichiometric and non-stoichiometric forms. Solvents such as water, acetone, ether, THF, methanol, ethanol, t-butanol, dioxane, isopropanol, isopropyl ether or mixtures thereof may be used.

In the addition to pharmaceutically acceptable salts, other salts are included in the invention. They may serve as intermediates in the purification of the compounds, in the preparation of other salts, or in the identification and characterization of the compounds or intermediates.

The compounds of formula (I) may be prepared in crystalline or non-crystalline form, and, if crystalline, may optionally be solvated, eg. as the hydrate. This invention includes within its scope stoichiometric solvates (eg. hydrates) as well as compounds containing variable amounts of solvent (eg. water).

The present invention also provides a process for the preparation of a compound of formula (I) or a pharmaceutically acceptable salt thereof which comprises of contacting a compound of formula (a) wherein all the substituents such as n, $R_1$, R and Ar are as defined for the compound of formula (I) earlier, with a sulfone derivative of formula (b):

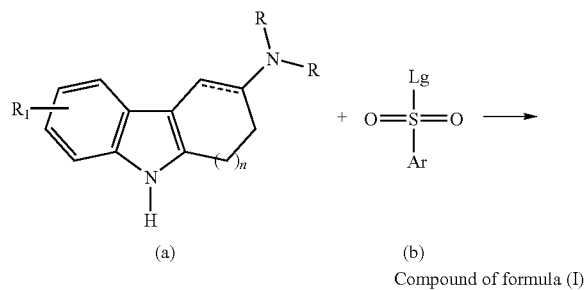

Compound of formula (I)

wherein, Ar are as defined for the compound of formula (I) earlier; and Lg represents as halogen atom (eg. fluoro, chloro or iodo); in presence of suitable base and inert solvent at suitable temperature to obtain a compound of formula (I).

The above reaction is preferably carried out in a solvent such as THF, toluene, DCM, acetone, water, DMF, DMSO, DME, and the like or a mixture thereof, and preferably using either acetone or DMF. The inert atmosphere may be maintained by using inert gases such as $N_2$, Ar or He. The reaction may be affected in the presence of a base such as $K_2CO_3$, $Na_2CO_3$, NaH or mixtures thereof. The reaction temperature may range from 0° C. to 100° C. based on the choice of solvent and preferably at a temperature in the range from 0° C. to 50° C. The duration of the reaction may range from 1 to 24 hours, preferably from 2 to 6 hours.

Compounds obtained by the above method of preparation of the present invention can be transferred to another compound of this invention by further chemical modifications of well-known reaction such as oxidation, reduction, protection, deprotection, rearrangement reaction, halogenation, hydroxylation, alkylation, alkylthiolation, demethylation, O-alkylation, O-acylation, N-alkylation, N-alkenylation, N-acylation, N-cyanation, N-sulfonylation, coupling reaction using transition metals and the like.

If necessary, any one or more than one of the following steps can be carried out,
i) converting a compound of the formula (I) into another compound of the formula (I)
ii) removing any protecting groups; or
iii) forming a pharmaceutically acceptable salt, solvate or a prodrug thereof.

In process (i), pharmaceutically acceptable salts may be prepared conventionally by reaction with the appropriate acid or acid derivative as described earlier in detail.

In process (ii), examples of protecting groups and the means for their removal can be found in T. W. Greene 'Protective Groups in Organic Synthesis' (J. Wiley and Sons, 1991). Suitable amine protecting groups include sulphonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric or trifluoroacetic acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—$COCF_3$) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid.

Process (iii) may be performed using conventional interconversion procedures such as epimerisation, oxidation, reduction, alkylation, nucleophilic or electrophilic aromatic substitution, ester hydrolysis or amide bond formation.

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable carriers. Thus, the active compounds of the invention may be formulated for oral, buccal, intranasal, parental (e.g., intravenous, intramuscular or subcutaneous) or rectal administration or a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer, or from a capsule using a inhaler or insufflator. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule it preferably should be in the form of powder. Capsules and cartridges (made, for example, from gelatin) for use in an inhaler or insufflator may be formulated containing a powder mix of a compound of the invention and a suitable powder base such as lactose or starch.

Aerosol formulations for treatment of the conditions referred to above (e.g., migraine) in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

An effective amount of a compound of general formula (I), or their derivatives as defined above can be used to produce a medicament, along with conventional pharmaceutical auxiliaries, carriers and additives.

Such therapy includes multiple choices: for example, administering two compatible compounds simultaneously in a single dose form or administering each compound individually in a separate dosage; or if required at same time interval or separately in order to maximize the beneficial effect or minimize the potential side-effects of the drugs according to the known principles of pharmacology.

The phrase "pharmaceutically acceptable" indicates that the substance or composition must be compatible chemically and/or toxicologically, with the other ingredients comprising a formulation, and/or the mammal being treated therewith.

The present compounds are useful as pharmaceuticals for the treatment of various conditions in which the use of a 5-$HT_6$ receptor antagonist is indicated, such as in the treatment of central nervous system disturbances such as psychosis, schizophrenia, manic depression, depression, neurological disturbances, memory disturbances. Parkinsonism, amylotrophic lateral sclerosis, Alzheimer's disease, Attention deficit hyperactivity disorder (ADHD) and Huntington's disease.

The term "schizophrenia" means schizophrenia, schizophreniform disorder, schizoaffective disorder and psychotic disorder wherein the term "psychotic" refers to delusions, prominent hallucinations, disorganized speech or disorganized or catatonic behavior. See Diagnostic and Statistical Manual of Mental Disorder, fourth edition, American Psychiatric Association, Washington, D.C.

The terms "treating", "treat", or "treatment" embrace all the meanings such as preventative, prophylactic and palliative.

"Therapeutically effective amount" is defined as 'an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein'.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors. A proposed dose of the active compounds of this invention, for either oral, parenteral, nasal or buccal administration, to an average adult human, for the treatment of the conditions referred to above, is 0.1 to 200 mg of the active ingredient per unit dose which could be administered, for example, 1 to 4 times per day.

For illustrative purposes, the reaction scheme depicted herein provides potential routes for synthesizing the compounds of the present invention as well as key intermediates. For a more detailed description of the individual reaction steps, see the Examples section. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Commercial reagents were utilized without further purification. Room temperature refers to 25-30° C. Melting points are uncorrected. IR spectra were taken using KBr and in solid state. Unless otherwise stated, all mass spectra were carried out using ESI conditions. $^1$H NMR spectra were recorded at 400 MHz on a Bruker instrument. Deuterated chloroform (99.8% D) was used as solvent. TMS was used as internal reference standard. Chemical shift values are expressed in parts per million (δ)-values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. NMR, mass were corrected for background peaks. Specific rotations were measured at room temperature using the sodium D (589 nm). Chromatography refers to column chromatography performed using 60-120 mesh silica gel and executed under nitrogen pressure (flash chromatography) conditions.

The following Descriptions and Examples illustrate the preparation of compounds of the invention.

Intermediate 1: 4-N,N-Dimethylamino cyclohexanone ethylene ketal

Procedure: To a solution of 10.0 gm (222.2 mM) dimethylamine in 50 ml methanol was added 5.0 gm (32.05 mM) 1,4-cyclohexanedione-mono ethylene ketal. The reaction mixture was stirred for 2 hours at room temperature. To this solution 4.02 gm (64.1 mM) sodium cyanoborohydride was added portion-wise in 15 mt. After addition was complete acetic acid was added to maintain the pH at about 6. When the addition of acetic acid no longer resulted in gas evolution, the reaction mixture was allowed to stir at room temperature for 18 hours. The reaction mixture was then concentrated under reduced pressure and the residual mass was partitioned between 1N sodium hydroxide and dichloromethane. Aqueous phase was further extracted with DCM. Separated organic layer. These organic phases were combined, dried over anhydrous sodium sulfate and concentrated under reduced pressure to give 5.0 gm (84%) of the desired compound.

IR spectra (cm$^{-1}$): 2945, 2874, 2776, 1448, 1282, 1159; Mass (m/z): 186.1 (M+H)$^+$; $^1$H-NMR (δ, ppm): 1.53-1.587 (4H, m), 1.76-1.81 (4H, m), 2.28 (7H, s), 3.94 (4H, s).

Intermediate 2: Dimethyl-(2,3,4,9-tetrahydro-1H-carbazole-3-yl)amine

Procedure: Aqueous sulphuric acid (10% w/v) solution 30 ml was taken in a round bottom flask, added 4-N,N-Dimethylamino cyclohexanone ethylene ketal (1.5 gm, 8.1 mM) followed by Phenyl hydrazine (1.52 gm, 14.08 mM) at room temperature. Then the reaction mass was heated to reflux temperature (95-100° C.) and maintained reflux for 2-3 hours. The progress of the reaction was monitored by TLC. After completion of reaction, the reaction mass was cooled to RT and then to 10-15° C. Then the mass was basified with aq. NaOH solution (20% w/v) and the aqueous layer was extracted with ethylacetate. Layers separated. Organic phase was washed with brine solution, dried over anhydrous sodium sulfate and removed solvent by distillation under vacuum. The residual mass was purified by flash chromatography (Ethylacetate:Triethylamine is 9:0.2).

IR spectra (cm$^{-1}$): 3141, 3054, 2921, 2831, 2729, 1626, 1591, 743; Melting range (° C.): 132.8-139.1; Mass (m/z): 214.9 (M+H)$^+$; $^1$H-NMR (δ, ppm): 1.80-1.91 (1H, m), 2.19-2.27 (1H, m), 2.42 (6H, s), 2.64-2.67 (1H, m), 2.78-2.83 (3H, m), 2.93-2.97 (1H, m), 7.05-7.13 (2H, m), 7.25-7.26 (1H, m) 7.45-7.46 (1H, db, m), 7.90 (1H, bs).

Example 1

(9-Benzenesulfonyl-2,3,4,9-tetrahydro-1H-carbazol-3-yl)dimethylamine

Procedure:

Taken potassium hydride 153.80 mg, 1.15 mM (30% suspension in mineral oil) in tetrahydrofuran (15 ml) and stirred at 25° C. for 10 mt. The reaction mixture was cooled to 10-15° C. Dimethyl-(2,3,4,9-tetrahydro-1H-carbazol-3-yl)amine (190 mg, 0.88 mM), dissolved in 5 ml of THF, was added slowly under stirring maintaining mass temperature below 25° C. The reaction mass was further stirred for 1 hour at 25° C. Then added a solution of Benzene sulphonyl chloride (235 mg, 1.33 mM, dissolved in 5 ml of THF) drop wise over a period of 15 mts. The reaction mass was stirred, while monitoring the progress of the reaction by TLC, for 2 hours at 25° C. After the completion of reaction, the mixture was diluted with 75 mL of ice water and extracted with ethyl acetate; Organic layer was washed with brine solution. The ethyl acetate extract was dried over anhydrous sodium sulfate; filtered and solvent was removed under reduced pressure to obtain the exude product. The residual mass was purified by flash chromatography (silica gel, EtoAc/n-Hexane, 9/1) to get the title compound, which was characterized by IR, NMR and mass spectral analyses.

IR spectra (cm$^{-1}$): 3065, 2933, 1630, 1370, 1172; Mass (m/z): 355 (M+H)$^+$; $^1$H-NMR (δ, ppm): 1.67-1.71 (1H, m), 1.96-2.08 (1H, m), 2.42 (6H, s), 2.51-2.6 (1H, m), 2.72-2.8 (1H, m) 2.82-3.0 (2H, m), 3.29-3.38 (1H, m), 7.23-7.28 (2H, m), 7.34-7.36 (1H, m), 7.39-7.43 (2H, m), 7.49-7.56 (1H, m), 7.75-7.77 (2H, m), 8.12-8.14 (1H, dd, J=8.06 Hz).

Example 2

9-[(4-Bromobenzenesulphonyl)-2,3,4,9-tetrahydro-1H-carbazol-3-yl]dimethylamine

Using essentially the same procedure described in example 1 and some non-critical variations the above derivative was prepared.

Melting range (° C.): 159.7-162.1; IR spectra (cm$^{-1}$): 3079, 2929, 1571, 1376, 1171; Mass (m/z): 433 (M+H)$^+$; $^1$H-NMR (δ, ppm): 1.67-1.71 (1H, m), 2.19-2.22 (1H, m), 2.39 (6H, s), 2.52-2.56 (1H, m), 2.68 (1H, m), 2.79-2.81 (1H, m), 2.83-2.84 (1H, m), 3.26-3.3 (1H, m), 7.24-7.27 (2H, m), 7.28-7.35 (1H, m), 7.52-7.54 (2H, m), 7.6-7.62 (2H, m), 8.09-8.11 (1H, m).

Example 3

9-[(4-Fluorobenzenesulphonyl)-2,3,4,9-tetrahydro-1H-carbazol-3-yl]dimethylamine

Using essentially the same procedure described in example 1 and some non-critical variations the above derivative was prepared.

Melting range (° C.): 130.2-132.8; IR spectra (cm$^{-1}$): 3098, 2942, 1588, 1376, 1177; Mass (m/z): 373 (M+H)$^+$; $^1$H-NMR (δ, ppm): 1.67-1.71 (1H, m), 2.20-2.23 (1H, m), 2.39 (6H, s), 2.52-2.55 (1H, m), 2.66-2.67 (1H, m), 2.79-2.84 (2H, m), 3.27-3.28 (1H, m), 7.05-7.10 (2H, m), 7.24-7.27 (2H, m), 7.34-7.35 (1H, m), 7.76-7.80 (2H, m), 8.10-8.12 (1H, m).

Example 4

9-[(4-Methylbenzenesulfonyl)-2,3,4,9-tetrahydro-1H-carbazol-3-yl]dimethylamine

Using essentially the same procedure described in example 1 and some non-critical variations the above derivative was prepared.

Melting range (° C.): 131.3; IR spectra (cm$^{-1}$): 3024, 2978, 2938, 1620, 1370, 1172; Mass (m/z): 369.4 (M+H)$^+$; $^1$H-NMR (δ, ppm): 1.67-1.71 (1H, m), 2.20-2.23 (1H, m), 2.33 (3H, s), 2.40 (6H, s), 2.52-2.56 (1H, m), 2.65-2.74 (1H, m), 2.80-2.85 (2H, m), 3.29-3.30 (1H, m), 7.18-7.27 (4H, m), 7.33-7.35 (1H, m), 7.64-7.66 (2H, m), 8.12-8.14 (1H, m).

Example 5

[9-(3-Chlorobenzenesulfonyl)-2,3,4,9-tetrahydro-1H-carbazol-3-yl]dimethylamine

Using essentially the same procedure described in example 1 and some non-critical variations the above derivative was prepared.

Melting range (° C.): 121.2; IR spectra (cm$^{-1}$): 3093, 3070, 2932, 1616, 1367, 1177; Mass (m/z): 389 (M+H)$^+$; $^1$H-NMR (δ, ppm): 1.69-1.73 (1H, m), 2.21-2.22 (1H, m), 2.53 (6H, s) 2.53-2.53 (1H, m), 2.68-2.69 (1H, m), 2.80-2.81 (1H, m), 2.84-2.85 (1H, m) 3.26-3.27 (1H, m), 7.25-729 (2H, m), 7.30-7.36 (2H, m), 7.46-7.50 (1H, m), 7.61-7.66 (1H, m), 7.67-7.76 (1H, m), 8.09-8.11 (1H, m).

Example 6

[9-(4-Isopropylbenzenesulfonyl)-2,3,4,9-tetrahydro-1H-Carbazol-3-yl]dimethylamine Using essentially the same procedure described in example 1 and some non-critical variations the above derivative was prepared.

Melting range (° C.): 162.4; IR spectra (cm$^{-1}$): 3068, 2928, 2962, 1621, 1364, 1170; Mass (m/z): 397.5 (M+H)$^+$; $^1$H-NMR (δ, ppm): 1.18-1.20 (6H, d, J=6.92), 1.69-1.72 (1H, m), 2.00-2.23 (2H, m), 2.40 (6H, s), 2.53-2.56 (1H, m), 2.66-2.74 (1H, m), 2.81-2.92 (2H, m), 3.30-3.30 (1H, m), 7.21-7.30 (4H, m), 7.31-7.37 (1H, m), 7.68-7.70 (2H, m), 8.13-8.15 (1H, m).

Example 7

[9-(3-Trifluoromethylbenzenesulfonyl)-2,3,4,9-tetrahydro-1H-carbazol-3-yl]dimethylamine Using essentially the same procedure described in example 1 and some non-critical variations the above derivative was prepared.

Melting range (° C.): 116.96; IR spectra (cm$^{-1}$): 3082, 2931, 1607, 1370, 1169; Mass (m/z): 423.3 (M+H)+; $^1$H-NMR (δ, ppm): 1.69-1.73 (1H, m), 2.22-2.23 (1H, m), 2.39 (6H, s) 2.53-2.56 (1H, m), 2.67-2.67 (1H, m), 2.79-2.84 (1H, m), 2.87-2.98 (1H, m), 3.28-3.29 (1H, m), 7.25-7.30 (2H, m), 7.34-7.37 (1H, m), 7.53-7.58 (1H, m), 7.76-7.79 (1H, m), 7.87-7.89 (1H, m), 8.13-8.15 (1H, bs), 8.10-8.12 (1H, d, J=8.08).

Example 8

[9-(4-Methoxybenzenesulfonyl)-2,3,4,9-tetrahydro-1H-carbazol-3-yl]-dimethylamine Using essentially the same procedure described in example 1 and some non-critical variations the above derivative was prepared.

Melting range (° C.): 138.81; IR spectra (cm$^{-1}$): 3096, 3032, 2937, 1593, 1367, 1166; Mass (m/z): 385.2 (M+H)+; $^1$H-NMR (δ, ppm): 1.66-1.73 (1H, m), 2.17-2.22 (1H, m), 2.39 (6H, s), 2.51-2.55 (1H, m), 2.66-2.67 (1H, m), 2.79-2.84 (1H, m), 2.86-2.96 (1H, m), 3.29-3.34 (1H, m), 3.79 (3H, s), 6.84-6.86 (2H, dd, J=7.0, 2.0 Hz), 7.22-7.27 (2H, m), 7.33-7.35 (1H, m), 7.70-7.72 (2H, dd, J=7.0, 2.0), 8.12-8.14 (1H, d, J=8.08).

Example 9

[6-Bromo-9-(benzenesulphonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3066, 2967, 2918, 2856, 1631, 1592, 1364, 1169; Mass (m/z): 433 (M+H)$^+$; $^1$H-NMR (δ, ppm): 1.68-1.71 (1H, m), 1.97-1.99 (1H, m), 2.39 (6H, s), 2.47-2.49 (1H, m), 2.69-2.75 (1H, m), 2.76-2.81 (1H, m), 2.85-2.96 (1H, m), 3.27-3.32 (1H, m), 7.35-7.38 (1H, dd, J=8.8, 1.9), 7.41-7.45 (2H, m), 7.47-7.48 (1H, d, J=1.9), 7.53-7.55 (1H, m), 7.73-7.75 (2H, m), 8.00-8.02 (1H, d, J=8.8).

Example 10

[6-Bromo-9-(4-bromobenzenesulphonyl)-2,3,4,9-tetrahydro-1H-Carbazol-3-yl]dimethylamine Using essentially the same procedure described in example 1 and some non-critical variations the above derivative was prepared.

IR spectra (cm$^{-1}$): 3088, 2927, 2862, 2822, 1592, 1373, 1170; Mass (m/z): 511, 513 (M+H)$^+$; $^1$H-NMR (δ, ppm): 1.66-1.71 (1H, m), 2.18-2.21 (1H, m), 2.37 (6H, s), 2.48-2.51 (1H, m), 2.65-2.77 (3H, m), 3.24-3.25 (1H, m), 7.36-7.38 (1H, dd, J=8.8, 1.92), 7.48-7.48 (1H, d, J=1.9 Hz), 7.54-7.60 (4H, m), 7.96-7.98 (1H, db, J=8.8).

Example 11

[6-Bromo-9-(4-fluorobenzenesulphonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3063, 2932, 2860, 2775, 1589, 1375, 1175; Melting range (° C.): 158.1-160.0; Mass (m/z): 450.7 (M+H)$^+$; $^1$H-NMR (δ, ppm): 1.67-1.71 (1H, m), 2.19-2.22 (1H, m), 2.37 (6H, s), 2.48-2.51 (1H, m), 2.65 (1H, m), 2.73-2.75 (1H, m), 2.77-2.78 (1H, m), 3.25-3.3 (1H, m), 7.08-7.12 (2H, m), 7.36-7.38 (1H, dd, J=8.84, 1.92), 7.48-7.49 (1H, d, J=1.88), 7.74-7.78 (2H, m), 7.97-8.00 (1H, d, J=8.84).

Example 12

[6-Bromo-9-(4-isopropylbenzenesulphonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3069, 2962, 2770, 1595, 1366, 1166; Melting range (° C.): 152.75-154.98; Mass (m/z): 475.2, 477.1 (M+H)$^+$; $^1$H-NMR (δ, ppm): 1.19-1.21 (6H, d, J=6.88), 1.66-1.71 (1H, m), 2.17-2.24 (1H, m), 2.37 (6H, s), 2.48-2.51 (1H, m), 2.65-2.65 (1H, m), 2.74-2.78 (1H, m), 2.87-2.93 (2H, m), 3.27-3.29 (1H, m), 7.25-7.33 (2H, m), 7.34-7.37 (1H, dd, J=8.8, 1.9), 7.48-7.48 (1H, d, J=1.92), 7.62-7.67 (2H, m), 7.97-8.00 (1H, d, J=8.84).

Example 13

[6-Bromo-9-(3-trifluoromethylbenzenesulphonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3105, 3082, 2936, 2820, 1606, 1594, 1372, 1175; Mass (m/z): 501.3, 503.2 (M+H)$^+$; $^1$H-NMR (δ, ppm): 1.68-1.73 (1H, m), 2.20-221 (1H, m), 2.37 (6H, s), 2.49-2.52 (1H, m), 2.64-2.64 (1H, m), 2.73-2.78 (1H, m), 3.25-3.26 (1H, m), 3.26-3.30 (1H, m), 7.37-7.40 (1H, dd, J=8.8, 1.9), 7.48-7.49 (1H, d, J=1.92), 7.55-7.59 (1H, m), 7.79-7.81 (1H, m), 7.85-7.87 (1H, m), 7.97-7.99 (1H, d, J=8.8), 8.04 (1H, bs).

Example 14

[6-Bromo-9-(2-bromobenzenesulphonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3086, 2920, 2772, 1614, 1594, 1363, 1163; Melting range (° C.): 158.78-161.04; Mass (m/z): 511.1, 513.1, 515.1 (M+H)$^+$; $^1$H-NMR (δ, ppm): 1.66-1.70 (1H, m), 2.13-2.17 (1H, m), 2.38 (6H, s), 2.55-2.58 (1H, m), 2.68-2.68 (1H, m), 2.72-2.79 (1H, m), 2.82-2.86 (1H, m), 3.1-3.14 (1H, m), 7.28-7.30 (1H, dd, J=8.8, 1.9), 7.40-7.43 (2H, m), 7.55-7.55 (1H, d, J=1.84), 7.68-7.74 (3H, m).

Example 15

[6-Bromo-9-(4-methoxybenzenesulphonyl)-2,3,4,9-tetrahydro-1H-carbazol-3-yl]dimethylamine Using essentially the same procedure described in example 1 and some non-critical variations the above derivative was prepared.

Mass (m/z): 463.1, 465.1 (M+H)$^+$; $^1$H-NMR (δ, ppm): 1.65-1.70 (1H, m), 2.18-2.21 (1H, m), 2.37 (6H, s), 2.47-2.50 (1H, m), 2.61-2.70 (1H, m), 2.73-2.78 (1H, m), 2.82-2.95 (1H, m), 3.27-3.31 (1H, m), 3.80 (3H, s), 6.86-6.88 (2H, dd, J=7.0, 2.0), 7.34-7.37 (1H, dd, J=8.8, 2.0 Hz), 7.46-7.47 (1H, d, J=1.88 Hz), 7.67-7.70 (2H, dd, J=8.96, 2.0 Hz), 7.79-8.01 (1H, d, J=8.8 Hz).

Example 16

[6-Chloro-9-benzenesulfonyl-2,3,4,9-tetrahydro-1H-carbazol-3-yl]dimethylamine

Using essentially the same procedure described in example 1 and some non-critical variations the above derivative was prepared.

IR spectra (cm$^{-1}$): 3052, 2936, 1619, 1369, 1170; Melting range (° C.): 150-155; Mass (m/z): 389.3, 391.2 (M+H)$^+$; $^1$H-NMR (δ, ppm): 1.72-1.76 (1H, m), 2.25-2.32 (1H, m), 2.47 (6H, s), 2.51-2.60 (1H, m), 2.81-2.92 (3H, m), 3.30-3.3 (1H, m), 7.22-7.25 (1H, dd, J=8.84, 2.12 Hz), 7.32-7.32 (1H, d, J=2.04), 7.42-7.46 (2H, m), 7.54-7.55 (1H, m), 7.73-7.75 (2H, m), 8.05-8.07 (1H, d, J=8.84).

Example 17

[6-Chloro-9-(3-trifluoromethylbenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3001, 3059, 2923, 1601, 1373, 1180; Mass (m/z): 457.2, 459.2 (M+H)$^+$; $^1$H-NMR (δ, ppm): 1.74-1.77 (1H, m), 2.28-2.29 (1H, m), 2.46 (6H, s), 2.57 (1H, m), 2.81-2.90 (3H, m), 3.29-3.33 (1H, m), 7.25-7.28 (1H, dd, J=8.0, 2.0), 7.33-7.34 (1H, d, J=2.04), 7.57-7.61 (1H, m), 7.80-7.82 (1H, m), 7.85-7.87 (1H, m), 8.02-8.05 (2H, m).

Example 18

[6-Chloro-9-(4-methylbenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3081, 3026, 2923, 1600, 1371, 1181; Melting range (° C.): 130-138; Mass (m/z): 403.3, 405.3 (M+H)$^+$; $^1$H-NMR (δ, ppm): 1.66-1.70 (1H, m), 2.19-2.22 (1H, m), 2.35 (3H, s), 2.38 (6H, s), 2.48-2.51 (1H, m), 2.67 (1H, m), 2.74-2.75 (1H, m), 2.82-2.98 (1H, m), 3.27-3.28 (1H, m), 7.20-7.23 (3H, m), 7.31-7.31 (1H, d, J=2.04), 7.62-7.64 (2H, m), 8.04-8.06 (1H, d, J=8.84).

Example 19

[6-Chloro-9-(4-bromobenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3078, 2927, 1593, 1376, 1168; Mass (m/z): 467, 469.0 (M+H)$^+$; $^1$H-NMR (δ, ppm): 1.70-1.75 (1H, m), 2.25-2.27 (1H, m), 2.44 (6H, s), 2.53-2.57 (1H, m), 2.80-2.87 (3H, m), 3.26-3.31 (1H, m), 7.2.3-7.25 (1H, dd, J=8.8, 1.7) 7.32-7.33 (1H, d, J=1.66), 7.54-7.63 (4H, m), 8.01-8.03 (1H, d, J=8.80).

Example 20

[6-Chloro-9-(4-fluorobenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 2933, 1590, 1492, 1454, 1377, 1173, 1068, 837, 586, 542; Melting range (° C.): 150-155; Mass (m/z): 407.3, 409.2 (M+H)$^+$; $^1$H-NMR (δ, ppm): 1.71-1.75 (1H, m), 2.25 (1H, m), 2.43 (6H, s), 2.54-2.54 (1H, m), 2.80-2.84 (3H, m), 3.27-3.29 (1H, m), 7.09-7.13 (2H, m), 7.23-7.26 (1H, m), 7.33-7.33 (1H, d, J=2.04 Hz), 7.74-7.78 (2H, m), 8.03-8.05 (1H, d, J=8.84).

Example 21

[6-Fluoro-9-benzenesulfonyl-2,3,4,9-tetrahydro-1H-carbazol-3-yl]dimethylamine

Using essentially the same procedure described in example 1 and some non-critical variations the above derivative was prepared.

IR spectra (cm$^{-1}$): 3058, 2964, 2825, 2777, 1603, 1371, 1172; Melting range (° C.): 127.7-130.3; Mass (m/z): 373.2; $^1$H-NMR (δ, ppm): 1.65-1.70 (1H, m), 2.18-2.21 (1H, m), 2.37 (6H, s), 2.48-2.53 (1H, m), 2.62-2.69 (1H, m), 2.72-2.78 (1H, m), 2.84-2.95 (1H, m), 3.27-3.28 (1H, m), 6.97-7.01 (2H, m), 7.41-7.4 (2H, m), 7.52-7.54 (1H, m), 7.73-7.75 (2H, m), 8.05-8.95 (1H, m).

Example 22

[6-Fluoro-9-(4-methylbenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3062, 2937, 2794, 1597, 1371, 1174; Melting range (° C.): 148.8-153; Mass (m/z): 387.3; $^1$H-NMR (δ, ppm): 1.65-1.70 (1H, m), 2.18-2.22 (1H, m), 2.35 (3H, s), 2.38 (6H, s), 2.44-2.52 (1H, m), 2.63-2.69 (1H, m), 2.72-2.79 (1H, m), 2.84-2.94 (1H, m), 3.27-3.28 (1H, m), 6.95-7.00 (2H, m), 7.19-7.21 (2H, d, J=8.2), 7.61-7.63 (2H, d, J=8.36), 8.05-8.08 (1H, m).

Example 23

[6-Fluoro-9-(4-isopropylbenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 2963, 2847, 2818, 1607, 1373, 1172; Melting range (° C.): 95.4-103.8; Mass (m/z): 415.4 (M+H)$^+$; $^1$H-NMR (δ, ppm): 1.19-1.20 (6H, d, J=6.96), 1.67-1.71 (1H, m), 2.19-2.22 (1H, m), 2.39 (6H, s), 2.46-2.54 (1H, m), 2.65-2.79 (2H, m), 2.88-2.97 (2H, m), 3.28-3.36 (1H, m), 6.96-7.01 (2H, m), 7.25-7.27 (2H, m), 7.65-7.67 (2H, m), 8.06-8.09 (1H, m).

Example 24

[6-Fluoro-9-(4-bromobenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3081, 2932, 2861, 1602, 1376, 1174; Melting range (° C.): 170.6-174.1; Mass (m/z): 451, 453.2 (M+H)$^+$; $^1$H-NMR (δ, ppm): 1.67-1.71 (1H, m), 2.19-2.23 (1H, m), 2.39 (6H, s), 2.46-2.54 (1H, m), 2.68-2.76 (2H, m), 2.82-2.93 (1H, m), 3.24-3.33 (1H, m), 6.97-7.01 (2H, m), 7.54-7.60 (4H, m), 8.02-8.06 (1H, m).

Example 25

[6-Fluoro-9-(4-fluorobenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3098, 2949, 2796, 1589, 1376, 1176; Melting range (° C.): 147.5-151.2; Mass (m/z): 391.3; $^1$H-NMR (δ, ppm): 1.67-1.72 (1H, m), 2.20-2.23 (1H, m), 2.39 (6H, s), 2.47-2.53 (1H, m), 2.69-2.78 (2H, m), 2.83-2.93 (1H, m), 3.26-3.27 (1H, m), 6.97-7.01 (2H, m), 7.07-7.12 (2H, m), 7.74-7.77 (2H, m), 8.03-8.07 (1H, m).

Example 26

[6-Methoxy-9-benzenesulfonyl-2,3,4,9-tetrahydro-1H-carbazol-3-yl]dimethylamine

Using essentially the same procedure described in example 1 and some non-critical variations the above derivative was prepared.

IR spectra (cm$^{-1}$): 3063, 2916, 2791, 1607, 1362, 1171; Melting range (° C.): 157.7-162; Mass (m/z): 385.3 (M+H)$^+$; $^1$H-NMR (δ, ppm): 1.62-1.69 (1H, m), 2.18-2.21 (1H, m), 2.38 (6H, s), 2.47-2.51 (1H, m), 2.65-2.65 (1H, m), 2.73-2.77 (1H, m), 2.82-2.94 (1H, m), 3.26-3.30 (1H, m), 3.83 (3H, s), 6.78-6.78 (1H, d, J=2.52), 6.86-6.88 (1H, d, J=9.0, 2.52), 7.38-7.42 (2H, m), 7.49-7.53 (1H, m), 7.72-7.74 (2H, m), 8.01-8.03 (1H, d, J=9.04).

Example 27

[6-Methoxy-9-(4-methylbenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3062, 2927, 2829, 2776, 1607, 1367, 1160; Melting range (° C.): 131.8-140.0; Mass (m/z): 399.2 (M+H)$^+$; $^1$H-NMR (δ, ppm): 1.66-1.70 (1H, m), 2.01-2.23 (1H, m), 2.33 (3H, s), 2.40 (6H, m), 2.44-2.52 (1H, m), 2.67-2.81 (2H, m), 2.83-2.94 (1H, m), 3.27-3.28 (1H, m), 3.83 (3H, s), 6.77-6.78 (1H, d, J=2.48), 6.85-6.88 (1H, d, J=9.0, 2.48), 7.17-7.19 (2H, d, J=8.24), 7.60-7.62 (2H, d, J=8.28), 8.00-8.03 (1H, d, J=9.05).

Example 28

[6-Methoxy-9-(4-methoxybenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3096, 2944, 2840, 1605, 1364, 1159; Mass (m/z): 415.2 (M+H)$^+$; $^1$H-NMR (δ, ppm): 1.65-1.7 (1H, m), 2.2-2.23 (1H, m), 2.4 (6H, s), 2.48-2.51 (1H, m), 2.64-2.72 (1H, m), 2.74-2.81 (1H, m), 2.83-2.93 (1H, m), 3.27-3.33 (1H, m), 3.78 (3H, s), 3.83 (3H, s), 6.77-6.78 (1H, d, J=2.80), 6.82-6.88 (3H, m), 7.65-7.69 (2H, m), 8.00-8.03 (1H, d, J=9.04).

Example 29

[6-Methoxy-9-(4-bromobenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3085, 2933, 2860, 2774, 1608, 1572, 1374, 1160; Melting range (° C.): 173.2-173.8; Mass (m/z): 463 (M+H)$^+$; $^1$H-NMR (δ, ppm): 1.62-1.72 (1H, m), 2.17-2.21 (1H, m), 2.38 (6H, s), 2.44-2.50 (1H, m), 2.63-2.65 (1H, m), 2.73-2.85 (2H, m), 3.24-3.49 (1H, m), 3.83 (3H, s), 6.78 (1H, bs), 6.86-6.88 (1H, m), 7.51-7.59 (4H, m), 7.99 (1H, d, J=8.92).

Example 30

[6-Methoxy-9-(4-fluorobenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3095, 2944, 2860, 2783, 1607, 1589, 1373, 1173; Melting range (° C.): 160.7-163.4; Mass (m/z): 403.3 (M+H)$^+$; $^1$H-NMR (δ, ppm): 1.65-1.70 (1H, m), 2.19-2.22 (1H, m), 2.39 (6H, s), 2.48-2.51 (1H, m), 2.62-2.69 (1H, m), 2.74-2.80 (1H, m), 2.81-2.92 (1H, m), 3.24-329 (1H, m), 3.83 (3H, s), 6.78-6.79 (1H, d, J=2.4), 6.86-6.89, (1H, dd, J=9.0, 2.5), 7.04-7.09 (2H, m), 7.72-7.76 (2H, m), 7.98-8.01 (1H, d, J=9.03).

Example 31

[6-Methoxy-9-(3-trifluoromethylbenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 3081, 2927, 1608, 1432, 1371, 1325, 1171, 1035, 573; Melting range (° C.): 144-146; Mass (m/z): 453.4 (M+H)$^+$; $^1$H-NMR (δ, ppm): 1.64-1.72 (1H, m), 2.21-2.24 (1H, m), 2-39 (6H, s), 2.49-2.52 (1H, m), 2.6-2.7 (1H, m), 2.73-2.78 (1H, m), 2.82-2.93 (1H, m), 3.25-3.32 (1H, m), 3.83 (3H, s), 6.783-6.789 (1H, d, J=2.52), 6.87-6.90 (1H, dd, J=9.0, 2.56), 7.51-7.55 (1H, t, J=7.92), 7.75-7.77 (1H, d, J=7.84), 7.83-7.85 (1H, d. J=7.91), 7.98-8.00 (1H, d, J=9.06), 8.01 (1H, bs).

Example 32

[6-Methylthio-9-benzenesulfonyl-2,3,4,9-tetrahydro-1H-carbazol-3-yl]dimethylamine Using essentially the same procedure described in example 1 and some non-critical variations the above derivative was prepared.

Melting range (° C.): 87.6; IR spectra (cm$^{-1}$): 2922, 1595, 1446, 1371, 1170, 1090, 723, 599; Mass (m/z): 401.3 (M+H)$^+$; $^1$H-NMR (δ, ppm): 1.67-1.7 (1H, m), 2.22-2.29 (1H, m), 2.43 (6H, s), 2.51 (3H, s), 2.52-2.57 (1H, m), 2.76-2.85 (3H, m), 3.29-3.33 (1H, m), 7.21-7.25 (2H, m), 7.40-7.44 (2H, m), 7.51-7.53 (1H, m), 7.73-7.75 (2H, m), 8.04-8.06 (1H, d, J=8.32).

Example 33

[6-Methylthio-9-(4-methylbenzenesulfonyl)-2,3,4,9-tetrahydro-1H-carbazol-3-yl]dimethylamine Using essentially the same procedure described in example 1 and some non-critical variations the above derivative was prepared.

IR spectra (cm$^{-1}$): 2917, 2771, 1595, 1369, 1168; Melting range (° C.): 105.2-115; Mass (m/z): 415.3 (M+H)$^+$; $^1$H-NMR (δ, ppm): 1.66-1.71 (1H, m), 2.2-2.23 (1H, m), 2.34 (3H, s), 2.4 (6H, s), 2.48 (3H, s), 2.51-2.55 (1H, m), 2.67-2.74 (1H, m), 2.78-2.93 (2H, m), 3.27-3.33 (1H, m), 7.18-7.23 (2H, m), 7.24-7.25 (2H, m), 7.61-7.64 (2H, m), 8.03-8.05 (1H, d, J=8.6).

Example 34

[6-Methylthio-9-(4-bromobenzenesulfonyl-2,3,4,9-tetrahydro-1H-carbazol-3-yl]dimethylamine Using essentially the same procedure described in example 1 and some non-critical variations the above derivative was prepared.

IR spectra (cm$^{-1}$): 3078, 2918, 2849, 2772, 1595, 1373, 1168; Melting range (° C.): 141.1-148.1; Mass (m/z): 479.3, 481.3 (M+H)$^+$; $^1$H-NMR (δ, ppm): 1.68-1.7 (1H, m), 2.0-2.23 (1H, m), 2.39 (6H, s), 2.51 (3H, s), 2.48-2.54 (1H, m), 2.63-2.71 (1H, m), 2.76-2.92 (2H, m), 3.23-3.32 (1H, m), 7.20-7.26 (2H, m), 7.53-7.55 (2H, m), 7.57-7.60 (2H, m), 8.00-8.02 (1H, d, J=8.6).

Example 35

[6-Methylthio-9-(4-Fluorobenzenesulfonyl-2,3,4,9-tetrahydro-1H-carbazol-3-yl]dimethylamine Using essentially the same procedure described in example 1 and some non-critical variations the above derivative was prepared.

IR spectra (cm$^{-1}$): 2924, 2824, 2776, 1589, 1373, 1171; Melting range (° C.): 148.9-156.1; Mass (m/z): 419.3 (M+H)$^+$; $^1$H-NMR (δ, ppm): 1.64-1.73 (1H, m), 2.19-2.21 (1H, m), 2.38 (6H, s), 2.48-2.52 (1H, m), 2.51 (3H, s), 2.61-2.69 (1H, m), 2.75-2.92 (2H, m), 3.24-3.25 (1H, m), 7.06-7.10 (2H, m), 7.21-7.26 (2H, m), 7.74-7.78 (2H, m), 8.01-8.03 (1H, d, J=8.6).

Example 36

[6-Chloro-9-(2-bromobenzenesulfonyl-2,3,4,9-tetrahydro-1H-carbazol-3-yl]dimethylamine Using essentially the same procedure described in example 1 and some non-critical variations the above derivative was prepared.

IR spectra (cm$^{-1}$): 2919, 1573, 1447, 1366, 1166, 956, 596; Mass (m/z): 466.8 (M+H)$^+$; $^1$H-NMR (δ, ppm): 1.66-1.71 (1H, m), 2.10-2.20 (1H, m), 2.39 (6H, s), 2.50-2.60 (1H, m), 2.65-2.80 (2H, m), 2.82-2.90 (1H, m), 3.10-3.18 (1H, m), 7.14-7.17 (1H, dd, J=8.84, 2.16), 7.394-7.399 (1H, J=2.0), 7.40-7.49 (2H, m), 7.68-7.73 (2H, m), 7.77-7.79 (1H, d, J=8.84).

Example 37

[6,8-Difluoro-9-(4-methylbenzenesulfonyl-2,3,4,9-tetrahydro-1H-carbazol-3-yl]dimethylamine Using essentially the same procedure described in example 1 and some non-critical variations the above derivative was prepared.

Melting range (° C.): 160-165; IR spectra (cm$^{-1}$): 3011, 2941, 1617, 1585, 1457, 1379, 1171, 959, 666, 607, 567; Mass (m/z): 405.3 (M+H)$^+$; $^1$H-NMR (δ, ppm): 1.68-1.80 (1H, m), 2.25-2.32 (1H, m), 2.39 (3H, s), 2.44 (6H, s), 2.49-2.60 (1H, m), 2.77-2.83 (2H, m), 3.05-3.15 (1H, m), 3.35-3.45 (1H, m), 6.65-6.71 (1H, m), 6.80-6.83 (1H, m), 7.25-7.27 (2H, d, J=8.16), 7.72-7.74 (2H, d, J=8.12).

Example 38

[6,8-Difluoro-9-(benzenesulfonyl-2,3,4,9-tetrahydro-1H-carbazol-3-yl]dimethylamine Using essentially the same procedure described in example 1 and some non-critical variations the above derivative was prepared.

Melting range (° C.): 150-155; IR spectra (cm$^{-1}$): 3021, 2925, 1617, 1585, 1461, 1377, 1172, 959, 720, 615, 575; Mass (m/z): 391.3 (M+H)$^+$; $^1$H-NMR (δ, ppm): 1.67-1.78

(1H, m), 2.25-2.30 (1H, m), 2.41 (6H, s), 2.48-2.55 (1H, m), 2.72-2.81 (2H, m), 3.07-3.15 (1H, m), 3.37-3.43 (1H, m), 6.66-6.71 (1H, dt, J=7.82, 2.32), 6.81-6.84 (1H, dd, J=7.82, 2.32), 7.47-7.52 (2H, m), 7.56-7.60 (1H, m), 7.84-7.86 (2H, m).

Example 39

[6-Bromo-9-(2,3-dichlorobenzenesulphonyl)-2,3,4,9-tetrahydro-1H-carbazol-3-yl]dimethylamine

Using essentially the same procedure described in example 1 and some non-critical variations the above derivative was prepared.

IR spectra (cm$^{-1}$): 2946, 2775, 1597, 1438, 1370, 1171, 795, 615; Melting range (° C.): 189-192; Mass (m/z): 501.4, 503.4 (M+H)$^{+}$; $^{1}$H-NMR (δ, ppm): 1.68-1.72 (1H, m), 2.15-2.18 (1H, m), 2.39 (6H, s), 2.50-2.60 (1H, m), 2.65-2.85 (3H, m), 3.1-3.2 (1H, m), 7.29-7.32 (1H, dd, J=8.82, 1.98), 7.33-7.37 (1H, t, J=8.11), 7.55-7.554 (1H, d, J=1.88), 7.67-7.69 (1H, dd, J=8.04, 1.43), 7.70-7.72 (1H, d, J=8.84), 7.76-7.78 (1H, dd, J=7.98, 1.39).

Example 40

[6-Methylthio-9-(2,3-dichlorobenzenesulfonyl-2,3,4,9-tetrahydro-1H-carbazol-3-yl]dimethylamine

Using essentially the same procedure described in example 1 and some non-critical variations the above derivative was prepared.

IR spectra (cm$^{-1}$): 2919, 1405, 1370, 1166, 793, 619, 600; Mass (m/z): 469.3, 471.3, 473.3 (M+H)$^{+}$; $^{1}$H-NMR (δ, ppm): 1.62-1.71 (1H, m), 2.15-2.18 (1H, m), 2.39 (6H, s), 2.51 (3H, s), 2.55-2.59 (1H, m), 2.66-2.70 (1H, m), 2.73-2.90 (2H, m), 3.10-3.20 (1H, m), 7.13-7.17 (1H, dd, J=8.68, 1.76), 7.30-7.35 (2H, m), 7.64-7.68 (1H, dd, J=8.12, 1.4), 7.70-7.75 (2H, m).

Example 41

[6-Methylthio-9-(4-methoxybenzenesulfonyl-2,3,4,9-tetrahydro-1H-carbazol-3-yl]dimethylamine

Using essentially the same procedure described in example 1 and some non-critical variations the above derivative was prepared.

IR spectra (cm$^{-1}$): 2926, 1594, 1456, 1363, 1261, 1157, 1087, 959, 800, 589, 554; Mass (m/z): 431.2 (M+H)$^{+}$; $^{1}$H-NMR (δ, ppm): 1.61-1.70 (1H, m), 2.18-2.26 (1H, m), 2.39 (6H, s), 2.48 (3H, s), 2.60-2.90 (4H, m), 3.25-3.35 (1H, m), 3.80 (3H, s), 6.84-6.88 (2H, m), 7.20-7.23 (1H, dd, J=8.6, 1.84), 7.24-7.25 (1H, d, J=1.61), 7.67-7.72 (2H, m), 8.03-8.06 (1H, d, J=8.6).

Example 42

[6-Methylthio-9-(3-chlorobenzenesulfonyl-2,3,4,9-tetrahydro-1H-carbazol-3-yl]dimethylamine

Using essentially the same procedure described in example 1 and some non-critical variations the above derivative was prepared.

IR spectra (cm$^{-1}$): 2919, 1579, 1458, 1370, 1168, 960, 796, 670, 559; Melting range (° C.): 87-89; Mass (m/z): 435.3, 437.5 (M+H)$^{+}$; $^{1}$H-NMR (δ, ppm): 1.70-1.80 (1H, m), 2.15-2.25 (1H, m), 2.40 (6H, s), 2.50-2.60 (4H, m), 2.65-2.75 (1H, m), 2.76-2.95 (2H, m), 3.24-3.30 (1H, m), 6.99-7.24 (2H, m), 7.33-7.38 (1H, t, J=7.96), 7.48-7.52 (1H, m), 7.58-7.62 (1H, m), 7.74-7.75 (1H, t, J=1.88), 8.00-8.02 (1H, d, J=8.64).

Example 43

Food Intake Measurement

Male Wistar rats (120-140 g) obtained from N.I.N. (National Institute of Nutrition, Hyderabad, India) were used. The chronic effect of the compounds of general formula (I) on food intake in well-fed rats was then determined as follows.

The rats were housed in their single home cages for 28 days. During this period, the rats were either dosed orally or i.p., with a composition comprising a compound of formula (I) or a corresponding composition (vehicle) without the said compound (control group), once-a-day. The rat is provided with ad libitum food and water.

On 0, 1$^{st}$, 7$^{th}$, 14$^{th}$, 21$^{st}$ and 28$^{th}$ day the rat is left with the pre-weighed amounts of food. Food intake and weight gain is measured on the routine basis. Also a food ingestion method is disclosed in the literature (Kask et al., European Journal of Pharmacology, 414, 2001, 215-224, and Turnball et. Al., Diabetes, vol 51, August, 2002, and some in-house modifications.).

Some representative compounds have shown the statistically significant decrease in food intake, when conducted in the above manner at the doses of either 10 mg/Kg, or 30 mg/Kg or both.

Example 44

Tablet Comprising a Compound of Formula (I)

| | |
|---|---|
| Compound according to example 1 | 5 mg |
| Lactose | 60 mg |
| Crystalline cellulose | 25 mg |
| K 90 Povidone | 5 mg |
| Pregelatinised starch | 3 mg |
| Colloidal silicon dioxide | 1 mg |
| Magnesium stearate | 1 mg |
| Total weight per tablet | 100 mg |

The ingredients are combined and granulated using a solvent such as methanol. The formulation is then dried and formed into tablets (containing about 20 mg of active compound) with an appropriate tablet machine.

Example 45

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Example 46

Liquid Oral Formulation

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 g |
| Colorings | 0.5 g |
| Distilled water | q.s. to 100 ml |

The ingredients are mixed to form a suspension for oral administration.

Example 47

Parenteral Formulation

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 48

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 49

Topical Formulation

| Ingredients | grams |
| --- | --- |
| Active compound | 0.2-2 g |
| Span 60 | 2 g |
| Tween 60 | 2 g |
| Mineral oil | 5 g |
| Petrolatum | 10 g |
| Methyl paraben | 0.15 g |
| Propyl paraben | 0.05 g |
| BHA (butylated hydroxy anisole) | 0.01 g |
| Water | 100 ml |

All of the ingredients, except water, are combined and heated to about 60° C. with stirring. A sufficient quantity of water at about 60° C. is then added with vigorous stirring to emulsify the ingredients, and water then added q.s. about 100 g.

Example 50

Object Recognition Task Model

The cognition-enhancing properties of compounds of this invention were estimated using a model of animal cognition: the object recognition task model. Male wistar rats (230-280 g) obtained from N.I.N. (National Institute of Nutrition, Hyderabad, India) were used as an experimental animal.

Four animals were housed in each cage. Animals were kept on 20% food deprivation before one day and given water ad libitum throughout the experiment and maintained on a 12 h light/dark cycle. Also the rats were habituated to individual arenas for 1 hour in absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase, (T1), the rats were placed individually in the open field for 3 min., in which two identical objects (plastic bottles, 12.5 cm height× 5.5 cm diameter) covered in yellow masking tape alone (a1 and a2) were positioned in two adjacent corners, 10 cm. from the walls. After 24 hour of the (T1) trial for long-term memory test, the same rats were placed in the same arena as they were placed in T1 trial. Choice phase (T2) rats were allowed to explore the open field for 3 min. in presence of one familiar object (a3) and one novel object (b) (Amber color glass bottle, 12 cm high and 5 cm in diameter. Familiar objects presented similar textures, colors and sizes. During the T1 and T2 trial, exploration of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed.

T1 is the total time spent exploring the familiar objects (a1+a2).

T2 is the total time spent exploring the familiar object and novel object (a3+b).

The object recognition test was performed as described by Ennaceur, A., Delacour, J., 1988, A new one-trial test for neurobiological studies of memory in rats—Behavioral data, Behav. Brain Res., 31, 47-59.

Representative compounds have shown positive effects indicating the increased novel object recognition viz; increased exploration time with novel object and higher discrimination index.

Example 51

Chewing/Yawning/Stretching Induction by $5HT_6R$ Antagonists

Male Wistar rats weighing 200-250 g were used. Rats were given vehicle injections and placed in individual, transparent chambers for 1 h each day for 2 days before the test day, to habituate them to the observation chambers and testing procedure. On the test day, rats were placed in the observation, chambers immediately after drug administration and observed continuously for yawning, stretching, and chewing behaviors from 60 to 90 min after drug or vehicle injections. 60 minutes prior to the drug administration Physostigmine, 0.1 mg/kg i.p. was administered to all the animals. Average number of yawns, stretches, and vacuous chewing movements during the 30 min observation period were recorded.

The representative examples demonstrated 40-60% increase in the stretching, yawning and chewing behaviors in comparison with the vehicle treated groups, at 1 mg/Kg, 3 mg/Kg, 10 mg/Kg and 30 mg/Kg. Reference: (a) King M. V., Sleight A., J., Woolley M. L., and et. Al. Neuropharmacology, 2004, 47, 195-204. (b) Bentey J. C., Bourson A., Boess F. G., Fone K. C. F., Marsden C. A., Petit N., Sleight A. J., British Journal of Pharmacology, 1999, 126 (7), 1537-1542).

Example 52

Water Maze

The water maze apparatus consisted of a circular pool (1.8 m diameter, 0.6 m high) constructed in black Perspex (TSE systems, Germany) filled with water (24±2° C.) and positioned underneath a wide-angled video camera to track animal. The 10 cm$^2$ perspex platform, lying 1 cm below the water surface, was placed in the centre of one of the four imaginary quadrants, which remained constant for all rats. The black Perspex used in the construction of the maze and platform offered no intramaze cues to guide escape behavior. By contrast, the training room offered several strong extramaze visual cues to aid the formation of the spatial map necessary for escape learning. An automated tacking system, [Videomot 2 (5.51), TSE systems, Germany] was employed. This program analyzes video images acquired via a digital camera and an image acquisition board that determined path length, swim speed and the number of entries and duration of swim time spent in each quadrant of the water maze. Reference: (a) Yamada N., Hattoria A., Hayashi T., Nishikawa T., Fukuda H. et. Al., Pharmacology, Biochem. And Behaviour, 2004, 78, 787-791. (b) Linder M. D., Hodges D. B>, Hogan J. B., Corsa J. A., et al The Journal of Pharmacology and Experimental Therapeutics, 2003, 307 (2), 682-691.

Example 53

Passive Avoidance

Animals were trained in a single-trial, step through, light-dark passive avoidance paradigm. The training apparatus consisted of a chamber 300 mm in length, 260 mm wide, and 270 mm in height, constructed to established designs. The front and top were transparent, allowing the experimenter to observe the behavior of the animal inside the apparatus. The chamber was divided into two compartments, separated by a central shutter that contained a small opening 50 mm wide and 75 mm high set close to the front of the chamber. The smaller of the compartments measured 9 mm in width and contained a low-power (6V) illumination source. The larger compartment measured 210 mm in width and was not illuminated. The floor of this dark compartment consisted of a grid of 16 horizontal stainless-steel bars that were 5 mm in diameter and spaced 12.5 mm apart. A current generator supplied 0.75 mA to the grid floor, which was scrambled once every 0.5 s across the 16 bars. A resistance range of 40-60 microohms was calculated for a control group of rats and the apparatus was calibrated accordingly. An electronic circuit detecting the resistance of the animal ensured an accurate current delivery by automatic variation of the voltage with change in resistance.

This experiment was carried out as described previously (Fox et al., 1995). Adult male Wistar tats weighing 200-230 g were used. Animals were brought to the laboratory 1 h before the experiment. On the day of training, animals were placed facing the rear of the light compartment of the apparatus. The timer was started once the animal has completely turned to face the front of the chamber. Latency to enter the dark chamber was recorded (usually <20 s), and having completely entered the dark compartment an inescapable foot shock of 0.75 mA for 3 s was administered to the animal. Animals were then returned to their home cages. Between each training session, both compartments of the chamber were cleaned to remove any confounding olfactory cues. Recall of this inhibitory stimulus was evaluated 24 h, 72 h and on 7 day post-training by returning the animal into the light chamber and recording their latency to enter the dark chamber, a criterion time of 300 s was employed. Some of the compounds showed significant increase in latency to reach the dark zone, at 10 mg/Kg oral dose. Reference: (a) Callahan P. M., Ilch C. P., Rowe N. B., Tehim A., Abst. 776. 19. 2004, Society for neuroscience, 2004. (b) Fox G. B., Connell A. W. U., Murphy K. J., Regan C. M., Journal of Neurochemistry, 1995, 65, 6, 2796-2799.

Example 54

Nova Screen Binding Assay for Human 5-HT$_6$ Receptor

Pharmacological data Compounds can be tested according to the following the procedures.
Materials and Methods:
Receptor source: Human recombinant expressed in HEK-293 cells
Radioligand: [$^3$H]LSD (60-80 Ci/mmol)
Final ligand concentration—[1.5 nM]
Non-specific determinant: Methiothepin mesylate—[0.1 μM]
Reference compound: Methiothepin mesylate
Positive control: Methiothepin mesylate
Incubation conditions: Reactions were carried out in 50 mM TRIS HCl (pH 7.4) containing 10 mM MgCl$_2$, 0.5 mM EDTA for 60 minutes at 37° C. The reaction was terminated by rapid vacuum filtration onto glass fiber filters. Radioactivity trapped onto the filters was determined and compared to control values in order to ascertain any interactions of test compound(s) with the cloned serotonin-5HT$_6$ binding site.

| S. no. | Example No. | IC$_{50}$ (nM) | Ki (nM) |
|---|---|---|---|
| 1 | 23 | 33.4 | 15.5 |
| 2 | 21 | 30.5 | 15.7 |
| 3 | 3 | 27 | 12.5 |
| 4 | 25 | 63.5 | 32.8 |
| 5 | 11 | 20.2 | 9.42 |
| 6 | 30 | 52.3 | 24.3 |
| 7 | 24 | 99.7 | 43.5 |
| 8 | 22 | 64.3 | 32.4 |
| 9 | 26 | 10.8 | 5.44 |
| 10 | 29 | 28.9 | 15.1 |
| 11 | 35 | 47.1 | 24.9 |
| 12 | 33 | 26.1 | 13.8 |
| 13 | 27 | 11.7 | 5.89 |

Reference: Monsma F. J. Jr., et al., Molecular Cloning and Expression of Novel Serotonin Receptor with High Affinity for Tricyclic Psychotropic Drugs. Mol. Pharmacol. (43): 320-327 (1993).

Example 55 cAMP Assay

The antagonist property of the compounds at the human 5-HT$_6$ receptors was determined by testing their effect on cAMP accumulation in stably transfected HEK-293 cells. Binding of an agonist to the human 5-HT$_6$ receptor will lead to an increase in adenyl cyclase activity. A compound that is an agonist will show an increase in cAMP production and a compound that is an antagonist will block the agonist effect.

Human 5-HT$_6$ receptors were cloned and stably expressed in HEK-293 cells. These cells were plated in 6 well plates in DMEM/F12 media with 10% fetal calf serum (FCS) and 500 ug/mL G418 and incubated at 37° C. in a CO$_2$ incubator. The cells were allowed to grow to about 70% confluence before initiation of the experiment. On the day of the experiment, the culture media was removed, and the cells were washed once with serum free medium (SFM). Two mL of SFM+IBMX media was added and incubated at 37° C. for 10 min. The media were removed and fresh SFM+IBMX media containing various compounds, and 1 uM serotonin (as antagonist) were added to the appropriate wells and incubated for 30 min. Following incubation, the media were removed and the cells were washed once with 1 mL of PBS (phosphate buffered saline). Each well was treated with 1 mL cold 95% ethanol and 5 mM EDTA (2:1) at 4° C. for 1 hour. The cells were then scraped and transferred into Eppendorf tubes. The tubes were centrifuged for 5 min at 4° C., and the supernatants were stored at 4° C. until assayed.

cAMP content was determined by EIA (enzyme-immunoassay) using the Amersham Biotrak cAMP EIA kit (Amersham RPN 225). The procedure used is as described for the kit. Briefly, cAMP is determined by the competition between unlabeled cAMP and a fixed quantity of peroxidase-labelled cAMP for the binding sites, on anti-cAMP antibody. The antibody is immobilized onto polystyrene microtitre wells precoated with a second antibody. The reaction is started by adding 50 uL, peroxidase-labeled cAMP to the sample (100 uL) preincubated with the antiserum (100 uL) for 2 hours at 4° C. Following 1 hour incubation at 4° C., the unbound ligand is separated by a simple washing procedure. Then an enzyme substrate, trimethylbenzidine (1), is added and incubated at room temperature for 60 min. The reaction is stopped by the addition of 100 uL 1.0 M sulphuric acid and the resultant color, read by a microtitre plate spectrophotometer at 450 nM within 30 minutes. In the functional adenylyl cyclase assay, some of the compound of this invention was found to be a competitive antagonist with good selectivity over a number of other receptors including other serotonin receptors such as 5-HT$_{1A}$ and 5-HT$_7$.

The invention claimed is:

1. A compound of formula (I),

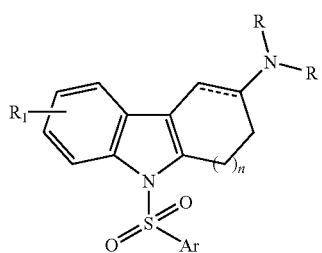

Formula (I)

or a pharmaceutically acceptable salt thereof wherein: '----' dashed line represents an optional double bond; Ar represents any one group selected from the group consisting of phenyl, naphthyl, monocyclic and bicyclic heteroaryl, each of which may be further substituted by one or more independent substituents defined as R$_1$;

R$_1$ represents one or multiple substitutions on a benzene ring wherein when there are multiple substituents, R$_1$ are the same or different, R$_1$ is selected from hydrogen, halogen, cyano, (C$_1$-C$_3$)alkyl, halo(C$_1$-C$_3$)alkyl, (C$_1$-C$_3$)alkoxy, halo(C$_1$-C$_3$)alkoxy, cyclo(C$_3$-C$_6$)alkyl and cyclo(C$_3$-C$_6$)alkoxy; R represents either hydrogen or (C$_1$-C$_3$)alkyl; n represents 1 or 2; or a pharmaceutically acceptable salt or stereoisomer thereof.

2. The compound as claimed in claim 1, wherein n is 1, and is represented by the formula

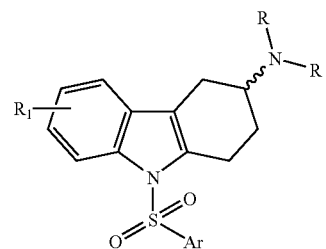

or a pharmaceutically acceptable salt thereof.

3. The compound as claimed in claim 1, wherein n is 1 and the double bond is as in the formula

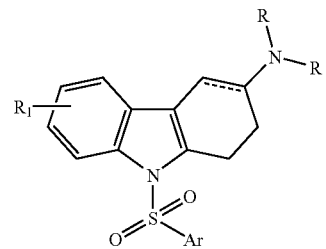

or a pharmaceutically acceptable salt thereof.

4. The compound as claimed in claim 1, wherein n is 2 and is represented by the formula

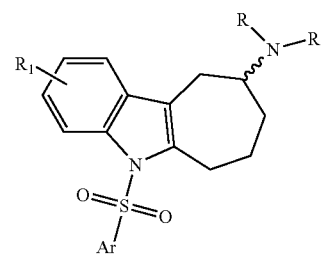

or a pharmaceutically acceptable salt thereof.

5. The compound as claimed in claim 1, wherein n is 2 and the double bond is as in the formula

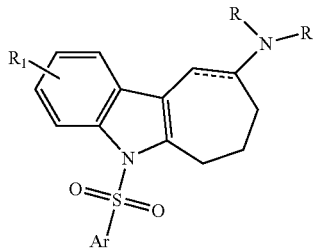

or a pharmaceutically acceptable salt thereof.

6. The compound as claimed in claim 1, wherein Ar is selected from the group consisting of is phenyl, naphthyl, indolyl, indazolyl, pyrrolopyridinyl, benzofuranyl, benzothienyl and benzimidazolyl.

7. The compound as claimed in claim 1, wherein $R_1$ is selected from the group consisting of hydrogen, halogen, perhaloalkyl, perhaloalkoxy, cyano, $(C_1-C_3)$alkyl, halo$(C_1-C_3)$alkyl, $(C_1-C_3)$alkoxy, halo$(C_1-C_3)$alkoxy, alkoxy$(C_1-C_3)$alkoxy, hydroxy$(C_1-C_3)$alkoxy, cyclo$(C_3-C_6)$alkyl and cyclo$(C_3-C_6)$alkoxy.

8. The compound as claimed in claim 1, selected from the group consisting of:

(9-Benzenesulfonyl-2,3,4,9-tetrahydro-1H-carbazol-3-yl)dimethylamine;
9-[(4-Bromobenzenesulphonyl)-2,3,4,9-tetrahydro-1H-carbazol-3-yl]dimethylamine;
9-[(4-Fluorobenzenesulphonyl)-2,3,4,9-tetrahydro-1H-carbazol-3-yl]dimethylamine;
9-[(4-Methylbenzenesulfonyl)-2,3 ,4,9-tetrahydro-1H-carbazol-3-yl]dimethylam ine;
[9-(3-Chlorobenzenesulfonyl)-2,3,4,9-tetrahydro-1H-carbazol-3-yl]dimethylamine;
[9-(4-Isopropylbenzenesulfonyl)-2,3,4,9-tetrahydro-1H-carbazol-3-yl]dimethylamine;
[9-(3-Trifluoromethylbenzenesulfonyl)-2,3,4,9-tetrahydro-1H-carbazol-3-yl]dimethylamine;
[9-(4-Methoxybenzenesulfonyl)-2,3,4,9-tetrahydro-1H-carbazol-3-yl]dimethylamine;
[6-Bromo-9-(benzenesulphonyl)-2,3,4,9-tetrahydro-1H-carbazol-3-yl]dimethylamine;
[6-Bromo-9-(4-bromobenzenesulphonyl)-2,3,4,9-tetrahydro-1H-carbazol-3-yl]dimethylamine;
[6-Bromo-9-(4-flourobenzenesulphonyl)-2,3,4,9-tetrahydro-1H-carbazol-3-yl]dimethylamine;
[6-Bromo-9-(4-isopropylbenzenesulphonyl)-2,3,4,9-tetrahydro-1H-carbazol-3-yl]dimethylamine;
[6-Bromo-9-(3-trifluoromethylbenzenesulphonyl)-2,3,4,9-tetrahydro-1H-carbazol-3-yl]dimethylamine;
[6-Bromo-9-(2-bromobenzenesulphonyl)-2,3,4,9-tetrahydro-1H-carbazol-3-yl]dimethylamine;
[6-Bromo-9-(4-methoxybenzenesulphonyl)-2,3,4,9-tetrahydro-1H-carbazol-3-yl]dimethylamine;
[6-Chloro-9-benzenesulfonyl-2,3,4,9-tetrahydro-1H-carbazol-3-yl]dimethylamine;
[6-Chloro-9-(3-trifluromethylbenzenesulfonyl)-2,3,4,9-tetrahydro-1H-carbazol-3-yl]dimethylamine;
[6-Chloro-9-(4-methylbenzenesulfonyl)-2,3,4,9-tetrahydro-1H-carbazol-3-yl]dimethylamine;
[6-Chloro-9-(4-bromobenzenesulfonyl)-2,3,4,9-tetrahydro-1H-carbazol-3-yl]dimethylamine;
[6-Chloro-9-(4-fluorobenzenesulfonyl)-2,3,4,9-tetrahydro-1H-carbazol-3-yl]dimethylamine;
[6-Fluoro-9-benzenesulfonyl-2,3,4,9-tetrahydro-1H-carbazol-3-yl]dimethylamine;
[6-Fluoro-9-(4-methylbenzenesulfonyl)-2,3 ,4,9-tetrahydro-1H-carbazol-3-yl]dimethylamine;
[6-Fluoro-9-(4-isopropylbenzenesulfonyl)-2,3,4,9-tetrahydro-1H-carbazol-3-yl]dimethylamine;
[6-Fluoro-9-(4-bromobenzenesulfonyl)-2,3,4,9-tetrahydro-1H-carbazol-3-yl]dimethylamine;
[6-Fluoro-9-(4-fluorobenzenesulfonyl)-2,3,4,9-tetrahydro-1H-carbazol-3-yl]dimethylamine;
[6-Methoxy-9-benzenesulfonyl-2,3,4,9-tetrahydro-1H-carbazol-3-yl]dimethylamine;
[6-Methoxy-9-(4-methylbenzenesulfonyl)-2,3,4,9-tetrahydro-1H-carbazol-3-yl]dimethylamine;
[6-Methoxy-9-(4-methoxybenzenesulfonyl)-2,3,4,9-tetrahydro-1H-carbazol-3 -yl]dimethylamine;
[6-Methoxy-9-(4-bromobenzenesulfonyl)-2,3,4,9-tetrahydro-1H-carbazol-3-yl]dimethylamine;
[6-Methoxy-9-(4-fluorobenzenesulfonyl)-2,3,4,9-tetrahydro-1H-carbazol-3-yl]dimethylamine;
[6-Methoxy-9-(3-trifluoromethylbenzenesulfonyl)-2,3,4,9-tetrahydro-1H-carbazol-3-yl]dimethylamine;
[6-Methylthio-9-benzenesulfonyl-2,3,4,9-tetrahydro-1H-carbazol-3-yl]dimethylamine;
[6-Methylthio-9-(4-methylbenzenesulfonyl)-2,3,4,9-tetrahydro-1H-carbazol-3-yl]dimethylamine;
[6-Methylthio-9-(4-bromobenzenesulfonyl-2,3,4,9-tetrahydro-1H-carbazol-3-yl]dimethylamine;
[6-Methylthio-9-(4-Fluorobenzenesulfonyl-2,3,4,9-tetrahydro-1H-carbazol-3-yl]dimethylamine;
[6-Chloro-9-(2-bromobenzenesulfonyl-2,3,4,9-tetrahydro-1H-carbazol-3-yl]dimethylamine;
[6,8-Difluoro-9-(4-methylbenzenesulfonyl-2,3,4,9-tetrahydro-1H-carbazol-3-yl]dimethylamine;
[6,8-Difluoro-9-(benzenesulfonyl-2,3,4,9-tetrahydro-1H-carbazol-3-yl]dimethylamine;
[6-Bromo-9-(2,3-dichlorobenzenesulphonyl)-2,3,4,9-tetrahydro-1H-carbazol-3-yl]dimethylamine;
[6-Methylthio-9-(2,3-dichlorobenzenesulfonyl-2,3,4,9-tetrahydro-1H-carbazol-3-yl]dimethylamine;
[6-Methylthio-9-(4-methoxybenzenesulfonyl-2,3,4,9-tetrahydro-1H-carbazol-3-yl]dimethylamine;
[6-Methylthio-9-(3-chlorobenzenesulfonyl-2,3,4,9-tetrahydro-1H-carbazol-3-yl]dimethylamine; a stereoisomer thereof ; and a salt thereof.

9. A process for preparing a compound of formula (I)

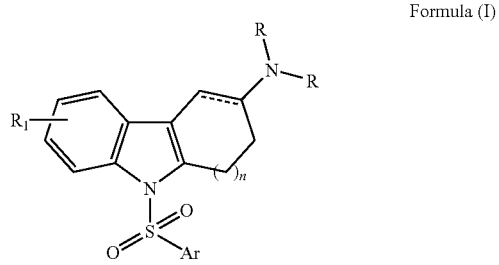

Formula (I)

or a pharmaceutically acceptable salt thereof, wherein: '----' dashed line represents an optional double bond; Ar represents any one group selected from the group consisting of phenyl, naphthyl, monocyclic and bicyclic heteroaryl, each of which may be further substituted by one or more independent substituents defined as $R_1$;

$R_1$ represents one or multiple substitutions on a benzene ring wherein when there are multiple substituents, the groups represented by $R_1$ are the same or different, $R_1$ is selected from hydrogen, halogen, cyano, $(C_1$-$C_3)$alkyl, halo$(C_1$-$C_3)$alkyl, $(C_1$-$C_3)$alkoxy, halo$(C_1$-$C_3)$alkoxy, cyclo$(C_3$-$C_6)$alkyl and cyclo$(C_3$-$C_6)$alkoxy; R represents either hydrogen or $(C_1$-$C_3)$alkyl; and n represents 1 or 2; or a pharmaceutically acceptable salt or stereoisomers thereof; said process comprising the steps of: contacting a compound of formula (a) wherein n, $R_1$, R and Ar are as defined for the compound of formula (I), with a sulfone derivative of formula (b):

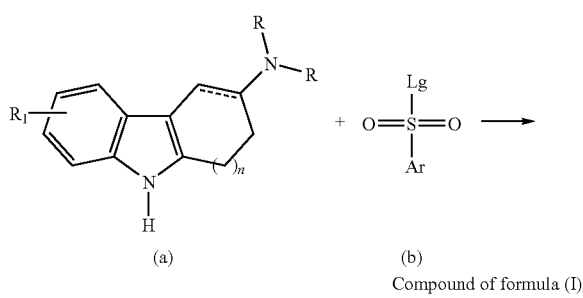

Compound of formula (I)

wherein, Ar is as defined for the compound of formula (I); and Lg represents a halogen atom, in the presence of a base and an inert solvent at ambient temperature to obtain a compound of formula (I).

10. The process as claimed in claim 9 further comprising one or more of:
 a) converting a compound of formula (I) into another compound of formula (I);
 b) removing any protecting groups; or
 c) forming a pharmaceutically acceptable salt, solvate or a prodrug thereof.

11. A pharmaceutical composition which comprises a pharmaceutically acceptable carrier and, an effective amount of a compound of formula (I) as defined in claim 1.

12. A pharmaceutical composition which comprises a pharmaceutically acceptable carrier and, an effective amount of a compound of formula (I) as defined in claim 8.

13. A method for treating a disorder of the central nervous system related to or affected by the 5-HT$_6$ receptor comprising administering to a patient having a disorder selected from the group consisting of Alzheimer's disease, Parkinson's disease, attention deficit disorder, obsessive compulsive disorder, stroke, head trauma, eating disorder and obesity, a therapeutically effect amount of a compound of Formula (I) as defined in claim 1.

\* \* \* \* \*